US007754865B2

(12) United States Patent
Supattapone et al.

(10) Patent No.: US 7,754,865 B2
(45) Date of Patent: Jul. 13, 2010

(54) COMPOSITIONS AND METHODS FOR ENHANCING THE IDENTIFICATION OF PRION PROTEIN PRP$^{Sc}$

(75) Inventors: Surachai Supattapone, Hanover, NH (US); Nathan R. Deleault, Lyme, NH (US)

(73) Assignee: Trustees of Dartmouth College, Hanover, NH (US)

( * ) Notice: Subject to any disclaimer, the term of this patent is extended or adjusted under 35 U.S.C. 154(b) by 345 days.

(21) Appl. No.: 10/553,591

(22) PCT Filed: May 5, 2004

(86) PCT No.: PCT/US2004/013883

§ 371 (c)(1),
(2), (4) Date: Jan. 17, 2006

(87) PCT Pub. No.: WO2004/110243

PCT Pub. Date: Dec. 23, 2004

(65) Prior Publication Data

US 2006/0127911 A1 Jun. 15, 2006

(51) Int. Cl.
*C07H 21/02* (2006.01)

(52) U.S. Cl. ...................... 536/23.1; 435/975
(58) Field of Classification Search ........................ None
See application file for complete search history.

(56) References Cited

U.S. PATENT DOCUMENTS

2002/0137114 A1  9/2002  Voelkel et al.

OTHER PUBLICATIONS

Saborio et al. ("Sensitive detection of pathological prion protein by cyclic amplification of protein misfolding" Nature. Jun. 14, 2001;411(6839):810-3).*
Stratagene ("Gene Characterization Kits" 1988).*
Mlzutani et al. (Virology. Sep 30, 2000;275(2):238-43).*
Van Ness et al. (Cell. Dec. 1979;18(4):1341-9.).*
Bessen et al., "Non-genetic propagation of strain-specific properties of scrapie prion protein", Nature 1995 375:698-700.
Brimacombe et al., "Characterization and polyanion-binding properties of purified recombinant prion protein", Biochem. J. 1999 342:605-613.
Caughey, B., "Formation of Protease-Resistant Prion Protein in Cell-Free Systems", Curr. Issues Mol. Biol. 2000 2(3):95-101.
Cordeiro et al., "DNA Converts Cellular Prion Protein into the β-Sheet Conformation and Inhibits Prion Peptide Aggregation", J. Biol. Chem. 2001 276(52):49400-49409.
Derrington et al., "PrP$^c$ has nucleic acid chaperoning properties similar to the nucleocapsid protein of HIV-1", C.R. Biologies 2002 325:17-23.
Gabus et al., "The Prion Protein Has RNA Binding and Chaperoning Properties Characteristic of Nucleocapsid Protein NCp7 of HIV-1", J. Biol. Chem. 2001 276(22):19301-19309.
Gabus et al., "The Prion Protein has DNA Strand Transfer Properties Similar to Retroviral Nucleocapsid Protein", J. Mol. Biol. 2001 307:1011-1021.
Horiuchi et al., "Specific binding of normal prion protein to the scrapie form via a localized domain initiates its conversion to the protease-resistant state", The EMBO Journal 1999 18(12):3193-3203.
Horiuchi et al., "Prion protein interconversions and the transmissible spongiform encephalopathies", Structure 1999 7(10):R231-R240.
Kocisko et al., "Species specificity in the cell-free conversion of prion protein to protease-resistant forms:A model for the scrapie species barrier", Proc. Natl. Acad. Sci. USA 1995 92:3923-3927.
Kocisko et al., "Cell-free formation of protease-resistant prion protein", Nature 1994 370:471-474.
Moscardini et al., "Functional Interactions of Nucleocapsid Protein of Feline Immunodeficiency Virus and Cellular Prion Protein with the Viral RNA", J. Mol. Biol. 2002 318:149-159.
Nandi et al., "DNA-induced Partial Unfolding of Prion Protein Leads to its Polymerisation to Amyloid", J. Mol. Biol. 2002 322:153-161.
Nandi et al., "Unusual Property of Prion Protein Unfolding in Neutral Salt Solution", Biochemistry 2002 41:11017-11024.
Proske et al., "Prion-Protein-Specific Aptamer Reduces PrP$^{Sc}$ Formation", ChemBioChem 2002 3:717-725.
Saborío et al., "Cell-Lysate Conversion of Prion Protein into Its Protease-Resistant Isoform Suggests the Participation of a Cellular Chaperone", Biochemical and Biophysical Research Communications 1999 258:470-475.
Weiss et al., "RNA Aptamers Specifically Interact with the Prion Protein PrP", Journal of Virology 1997 71(11):8790-8797.
Zeiler et al., "Concentration and removal of prion proteins from biological solutions", Biotechnol. Appl. Biochem. 2003 37:137-182.

\* cited by examiner

*Primary Examiner*—Christopher M. Babic
(74) *Attorney, Agent, or Firm*—Licata & Tyrrell P.C.

(57) ABSTRACT

The present invention provides compositions, methods and kits for enhancing the amplification of PrP$^{sc}$ for use in increasing the sensitivity of identifying the presence of PrP$^{sc}$ in a sample.

**2 Claims, No

COMPOSITIONS AND METHODS FOR ENHANCING THE IDENTIFICATION OF PRION PROTEIN PrP$^{Sc}$

This invention was made in the course of research sponsored by the National Institutes of Health (NIH Grant No. K08 NS02048-04). The U.S. government may have certain rights in this invention.

BACKGROUND OF THE INVENTION

Infectious agents of prion diseases, such as Creutzfeldt Jakob Disease (CJD), are devoid of nucleic acid and instead are composed of a specific infectious protein (Prusiner (1982) *Science* 216:136-44). This protein, PrP$^{Sc}$, appears to be generated by the template-induced conformational change of a normally expressed neuronal glycoprotein, PrP$^C$ during the course of disease (Prusiner, S. B. (ed.) *Prion Biology and Diseases*, Cold Spring Harbor Laboratory Press, Cold Spring Harbor, N.Y. (1999). While numerous studies have established the conversion of PrP$^C$ to PrP$^{Sc}$ as the central pathogenic event of prion disease, cellular factors other than PrP$^C$ which may be involved in the efficient catalysis of PrP$^{Sc}$ are unknown (Aguzzi and Weissmann *Nature* 389:795-8).

Various methods have been developed to enhance the amplification of PrP$^{Sc}$ to increase the sensitivity of detecting PrP$^{Sc}$ Saborio, et al. ((2001) *Nature* 411:810-3) disclose the use of a protein misfolding cyclic amplification (PMCA) method wherein prion-infected tissue homogenates containing PrP$^C$ are combined with normal brain homogenates in the presence of TRITON® X-100 and sodium dodecyl sulfate and subjected to repeated cycles of incubation and sonication to convert PrP$^C$ in normal tissue to PrP$^{Sc}$. Lucassen, et al. ((2003) *Biochemistry* 42:4127-35) disclose a modified version of the PMCA method wherein the normal and prion-infected tissue homogenates are incubated under non-denaturing conditions for the conversion of PrP$^C$ in normal tissue to PrP$^{Sc}$. Further, purified proteins and cell-lysate systems have been used to convert PrP$^C$ to PrP$^{Sc}$ (Caughey, et al. (2000) *Curr Issues Mol Biol* 2(3):95-101; Horiuchi and Caughey (1999) Structure Fold Des. 7:R231-R240; Saborio et al. (1999) *Biochem Biophys Res Commun* 258:470-475). Optimal non-denaturing, cell-free conditions (KCl, MgCl$_2$, citrate buffer and sarkosyl) for the conversion of PrP$^C$ to PrP$^{Sc}$ have also been disclosed (Horiuchi and Caughey (1999) *EMBO J.* 18:3193-3203). Cordeiro, et al. ((2001) *J. Biol. Chem.* 276:49400-9) teach that sequence-specific DNA binding to recombinant murine prion protein converts it from PrP$^c$ to the soluble PrP$^{Sc}$ isoform similar to that found in the fibrillar state. Further, Nandi et al. ((2002) *Biochemistry* 41:11017-11024) teach that the interaction between PrP$^c$ and anions (sulfate/phosphate) in polyionic ligands such as sulfated glycosaminoglycan and DNA, induce unfolding of the prion protein and conversion to PrP$^{Sc}$. DebBurman, et al. ((1997) *Proc. Natl. Acad. Sci. USA* 94(25):13938-43) demonstrate that GroEL and Hsp104 (heat shock protein 104), significantly, but distinctly affect conversion of PrP$^c$ to PrP$^{Sc}$.

Similarly, nucleic acids have been shown to bind to and promote the conformational change of recombinant PrP (Derrington, et al. (2002) *C R Acad. Sci. III* 325:17-23; Moscardini, et al. (2002) *J. Mol. Biol.* 318:149-59; Gabus, et al. (2001) *J. Biol. Chem.* 276:19301-9; Gabus, et al. (2001) *J. Mol. Biol.* 307:1011-21; Proske, et al. (2002) *Chembiochem* 3:717-25; Weiss, et al. (1997) *J. Virol.* 71:8790-7; Zeiler, et al. (2003) *Biotechnol. Appl. Biochem.* 37:173-82; Nandi et al. (2002) *J. Mol. Biol.* 322:153-61; Brimacombe, et al. (1999) *Biochem. J.* 342:605-613).

Purified PrP$^C$ also converts into protease-resistant PrP$^{Sc}$ in vitro in the absence of cellular cofactors (Kocisko, et al. (1995) *Nature* 370:471-4) and, thus, the PrP molecules themselves are sufficient to drive species- and strain-specific PrP$^{Sc}$ formation in vitro (Bessen, et al. (1995) *Nature* 375:698-700; Kocisko, et al. (1995) *Proc. Natl. Acad. Sci. USA* 92:3923-7). However, a 50-fold molar excess of purified PrP$^{Sc}$ is required to drive conversion of purified PrP$^C$, suggesting that optimal efficiency of amplification may depend on the presence of cellular factors other than PrP$^C$ (Caughey, et al. (1999) *Methods Enzymol.* 309:122-33). Transgenic experiments in mice and cultured cells also suggest that prion formation requires a catalytic factor "X" that has high affinity for positively charged residues at the C- and N-termini of PrP (Telling, et al. (1995) *Cell* 83:79-90; Kanecko, et al. (1997) *Proc. Natl. Acad. Sci. USA* 94:10069-74; Zulianello, et al. (2000) *J. Virol.* 74:4351-60; Perrier, et al. (2002) *Proc. Natl. Acad. Sci. USA* 99:13079-84).

While PrP$^{Sc}$ detection limits of 2 pM, corresponding to an aggregate concentration of approximately 2 fM (Bieschke, et al. (2000) *Proc. Natl. Acad. Sci. USA* 97(10):5468-73) to 50 pg PrP$^{Sc}$ (Barnard, et al. (2000) *Luminescence* 15: 357-362) have been reported using immunoassays, improved methods of increasing the detection limits are needed to enhance the detection limits of these assays so that prion diseases may be detected at the earliest possible stages of development. It has now been found that amplification of PrP$^{Sc}$ in vitro involves an RNA molecule that is useful for increasing the sensitivity of diagnostic methods for detecting PrP$^{Sc}$.

SUMMARY OF THE INVENTION

One aspect of the present invention is a ribonucleic acid (RNA) molecule for use in enhancing the amplification of PrP$^{Sc}$. This enhancement is useful for increasing the detection limits of assays for diagnosing prion-associated diseases.

Another aspect of the present invention is a method for identifying the presence of PrP$^{Sc}$. The method involves contacting a sample suspected of containing an infectious prion with an RNA molecule which enhances the amplification of PrP$^{Sc}$ and identifying the presence of the PrP$^{Sc}$.

Kits for identifying the presence of PrP$^{Sc}$ are also provided.

DETAILED DESCRIPTION OF THE INVENTION

It has been shown that a modified version of the PMCA method could be used to amplify PrP$^{Sc}$ in vitro without sonication or SDS in a species- and strain-specific manner (Lucassen, et al. (2003) supra). In this method, diluted prion-infected brain homogenate (0.1% w/v) is mixed either with 5% (w/v) normal brain homogenate (relative ratio 1:50) or buffer control and incubated overnight at 37° C. Hamster Sc237 PrP$^{Sc}$ is typically amplified ~6-fold under these conditions. It has now been found that, under similar PrP$^{Sc}$ amplification reactions, treatment of homogenate with DNase-free pancreatic RNase abolishes PrP$^{Sc}$ amplification in a dose-dependent manner. In vitro PrP$^{Sc}$ amplification was also abolished by purified RNase A, which degrades RNA through cleavage at pyrimidine residues (Volkin and Cohn (1953) *J. Biol. Chem.* 205:767), and by RNase T1, which specifically cleaves RNA molecules at guanine residues (Sato-Asano (1959) *J. Biochem. (Tokyo)* 46:31). Non-specific nucleases such as micrococcal nuclease and benzonase also inhibited PrP$^{Sc}$ amplification.

In contrast, PrP$^{Sc}$ amplification was not affected by addition of RNase V1, which degrades double-stranded RNA molecules (Lockard and Kumar (1981) *Nucl. Acids Res.*

9:5125-40) or RNase H, which specifically cleaves RNA:DNA hybrids (Banks (1974) *Euro. J. Biochem.* 47:499-507). These results indicate that a single-stranded RNA is involved in the amplification of PrP$^{Sc}$ in vitro. Addition of DNase or the restriction enzyme EcoRI did not decrease PrP$^{Sc}$ amplification, indicating that DNA is not required for this process. Addition of apyrase and heparinase III also had no effect on PrP$^{Sc}$ amplification, indicating that neither of these high-energy nucleotides nor molecules containing heparan sulfate are required for PrP$^{Sc}$ amplification in vitro.

Levels of PrP$^C$ and PrP$^{Sc}$ were measured after an overnight incubation with the various nuclease preparations to determine whether the nuclease preparations were contaminated with proteases. These measurements confirmed that levels of PrP$^C$ and input PrP$^{Sc}$ were both unperturbed by addition of enzymes that inhibited PrP$^{Sc}$ amplification.

As a control to confirm that abolition of PrP$^{Sc}$ amplification was dependent upon catalytic activity of each inhibitory nuclease, benzonase, micrococcal nuclease and RNase A were added to PrP$^{Sc}$ amplification reactions in an enzymatically inactive states. Both benzonase and micrococcal nuclease require divalent cations for enzymatic activity, thus these nucleases were inactivated by the addition of 5 mM EDTA. The active site of RNase A contains a critical histidine residue that is covalently modified by diethyl pyrocarbonate (DEPC). Therefore, RNase A was pretreated with DEPC to inhibit the ribonuclease activity of RNase A. Excess DEPC was subsequently removed by dialysis. The results of these experiments indicated that none of the three nucleases inhibited PrP$^{Sc}$ amplification in their inactive states and that intact RNA molecules catalyze this process.

Both RNase A and RNase T1 cleave RNA by a chemical mechanism involving the formation of a 2',3'-cyclic phosphate intermediate. RNase A digestion ultimately generates pyrimidine 3'-monophosphate products (Volkin and Cohn (1953) supra), while RNase T1 digestion yields 2',3'-cyclic guanosine monophosphate (GMP) end-products (Sato-Asano (1959) supra). The effect of cyclic 2',3'-GMP and 3'-cytidine monophosphate (CMP) on PrP$^{Sc}$ amplification were measured to ascertain whether the inhibitory effect of the RNase enzymes was attributable to inhibition by accumulated end-products. Neither of these nucleotides inhibited PrP$^{Sc}$ amplification in vitro at concentrations up to 1 mM. Control experiments negated the possibilities that contaminating proteases, steric hindrance, or digestion of end-products accounted for the inhibition of PrP$^{Sc}$ amplification by specific nucleases. Thus, RNA is involved in PrP$^{Sc}$ amplification in vitro.

Isolated RNA molecules were analyzed for the ability to amplify PrP$^{Sc}$ from nuclease-treated normal brain homogenates. Total RNA isolated from hamster brain successfully reconstituted the ability of benzonase-pretreated brain homogenate to amplify PrP$^{Sc}$ in a dose-dependent manner. In contrast, purified heparan sulfate proteoglycan failed to reconstitute PrP$^{Sc}$ amplification. Other polyanions, such as single-stranded DNA, polyadenylic acid, and polyglutamic acid also failed to reconstitute PrP$^{Sc}$ amplification.

The molecular size of the RNA species which enhances PrP$^{Sc}$ amplification was determined by fractionating a preparation of total hamster brain RNA by ultrafiltration through a filter with a molecular weight cutoff ~100,000. Using agarose gel electrophoresis, it was determined that the ribosomal RNA (rRNA) bands were observed in the retentate and the transfer RNA (tRNA) in the filtrate. Using these samples, it was found that the filter retentate, but not the filtrate, enhanced PrP$^{Sc}$ amplification. In similar experiments, total RNA was separated using oligo dT column chromatography and sucrose gradient separation. RNA which enhanced PrP$^{Sc}$ amplification was primarily found in the poly A– fraction from the oligo dT column chromatography and, upon size separation by sucrose gradient, was determined to be more than 1.49 kb in size; however, the RNA molecule did not appear to be a ribosomal RNA subunit. These data indicate that the RNA species responsible for catalyzing PrP$^{Sc}$ amplification or conversion is greater than 100,000 molecular weight (>300 nucleotides) and may not contain a poly-adenine tail.

In reconstitution experiments, nuclease pretreatment of endogenous RNA was incomplete because these digestion reactions were carried out at 4° C. to avoid denaturing PrP$^C$ prior to the addition of polyanions. Thus, it was determined whether the addition of total hamster brain RNA could increase the efficiency of PrP$^{Sc}$ amplification in vitro in brain samples which were not pretreated with nuclease. In these studies, a more dilute homogenate of prion-infected brain (0.02% w/v) was mixed overnight with 5% (w/v) normal brain homogenate (relative ratio 1:250) without sonication and PrP$^{Sc}$ amplification was subsequently measured. These results indicated that addition of total hamster brain RNA to this mixture of intact brain homogenates significantly stimulated PrP$^{Sc}$ amplification over baseline. As a control, input PrP$^{Sc}$ or PrP$^C$ in these samples was measured to confirm that addition of RNA did not alter the levels of PrP$^{Sc}$ or PrP$^C$.

Specificity of RNA-mediated stimulation of PrP$^{Sc}$ amplification was determined by isolating total RNA from several sources, including *E. coli, S. cerevisiae, C. elegans, D. melanogaster*, and mouse and hamster brain. Agarose gel electrophoresis analysis of these preparations revealed the expected band patterns for each species and confirmed that each preparation contained high-quality, non-degraded RNA. Furthermore, each of these preparations was substantially free from contaminants as judged by optical spectroscopy ($OD_{260}/OD_{280}$>1.9). Unexpectedly, among the preparations of RNA tested, only hamster and mouse brain RNA stimulated PrP$^{Sc}$ amplification in vitro. This species-specificity was not attributed to tissue-specificity because total hamster liver RNA also stimulated PrP$^{Sc}$ amplification. Thus, mice and hamsters express specific RNA molecules involved in PrP$^{Sc}$ amplification.

The utility of exogenously supplying RNA to a standard amplification method was determined. Accordingly, amplification of PrP$^{Sc}$ by the PMCA technique (Saborio, et al. (2001) supra) was measured in the presence and absence of supplemental RNA. These results showed that addition of total hamster brain RNA increased the PrP$^{Sc}$ signal obtained by eight sonication cycles of PMCA by ~10-fold, and that more PrP$^{Sc}$ was detected at every sonication cycle when additional RNA was present.

To isolate the RNA species which enhances PrP$^{Sc}$ amplification, it was determined whether PrP$^C$ could be purified and used as a substrate for PrP$^{Sc}$ amplification. It was found that the purified PrP$^C$ could be used as a substrate for amplification of PrP$^{Sc}$ and this amplification was sensitive to RNase A and could be stimulated by RNA from hamster brain. Therefore, the stimulatory RNA species bind tightly to the purified PrP$^C$ and purified PrP$^C$ can be used to purify the RNA species which enhance PrP$^{Sc}$ amplification. The RNA species are purified by mixing total brain RNA with purified PrP$^C$ so that the RNA species of interest bind to the PrP$^C$ protein. The RNA/PrP$^C$ ribonucleoprotein complex is then purified by coimmunoprecipitation or affinity chromatography using an anti-PrP antibody. The RNA molecule(s) is then converted to a cDNA using, for example, random primers and reverse transcriptase and the nucleotide sequence determined.

Accordingly, one aspect of the present invention is an RNA molecule which enhances, increases, or stimulates the amplification of $PrP^{Sc}$. The term "RNA molecule" as used herein is intended to include one or more different ribonucleic acid sequences which enhance the amplification of $PrP^{Sc}$. Preferably, the RNA molecule is more than 300 nucleotides in length, more preferably 1000 nucleotides in length, and most preferably 1500 nucleotides in length. The RNA molecule may be purified using any standard method or part of a complex mixture of RNA molecules and may be obtained from a natural source or synthesized. The RNA molecule may be obtained preferably from vertebrates including mammals such as humans, bovine, ovine, felines, canines, deer, elk, mice, hamsters, mink and the like. Other vertebrates from which the RNA molecule may be obtained include fish or birds. Alternatively, the RNA molecule may be synthesized from a DNA template such as a genomic DNA or cDNA template by in vitro, in situ, or in vivo transcription or may be produced by an automated RNA synthesizer. The RNA molecule may be the entire RNA molecule or an active fragment thereof which retains the capacity for enhancing the amplification of $PrP^{Sc}$.

If synthesized, the RNA molecule may contain modified backbones or non-natural internucleoside linkages to increase stability or decrease degradation. For example, the RNA molecule may have a modified backbone which contains phosphorothioates, chiral phosphorothioates, phosphorodithioates, phosphotriesters, aminoalkylphosphotriesters, methyl and other alkyl phosphonates, short chain alkyl or cycloalkyl internucleoside linkages, mixed heteroatom and alkyl or cycloalkyl internucleoside linkages, or one or more short chain heteroatomic or heterocyclic internucleoside linkages and the like. Alternatively, the RNA molecule may be have both the sugar and the internucleoside linkage, i.e., the backbone, of the nucleotide units replaced with novel groups (e.g., a peptide nucleic acid (PNA)). Other such modifications which increase the stability or decrease the degradation of RNA are well-known to those of skill in the art.

$PrP^C$, as used herein, is defined as the naturally expressed glycoprotein $PrP^C$, also known as PrP-sen, which is found in the neurons of mammals. Not to be held to any particular mechanism of action, it is believed that contact between $PrP^C$ and an infectious prion or $PrP^{Sc}$ brings about a conformational change in $PrP^C$, converting it from a protein primarily composed of alpha-helices to a protein primarily composed of beta-sheets. This conversion creates a protease resistant, prion protein (i.e., $PrP^{Sc}$, PrP-res) associated with a prion disease. While the presence of $PrP^{Sc}$ is correlated with a prion-associated disease, the skilled artisan may appreciate that $PrP^{Sc}$ may or may not be the causative agent of a prion-associated disease. Hence, the term "infectious prion" is intended to mean a prion which causes a prion-associated disease.

Another aspect of the present invention is a method for identifying the presence of $PrP^{Sc}$ in a sample by enhancing the amplification of $PrP^{Sc}$ and identifying the presence of $PrP^{Sc}$. The first step of the method involves contacting a sample suspected of containing an infectious prion protein with an RNA molecule which enhances the amplification of $PrP^{Sc}$. In this step of the method, $PrP^{Sc}$ may be converted from $PrP^C$ which is endogenous to the sample and has yet to be converted to $PrP^{Sc}$ or may preferably be supplied exogenously as an isolated protein, mixture of proteins, or homogenate.

A sample is intended to include biological material, e.g., blood, plasma, serum, cell products, cell extracts, cerebrospinal fluid (CSF), tissue homogenates, urine, semen, and combinations thereof as well as environmental materials, e.g., soil and water, and food samples including canned goods, meats, and animal fodder. A sample suspected of containing an infectious prion is one which may have come in contact with an infectious prion protein or one from an individual that may be predisposed (e.g., having inherited) or at risk of having or acquiring (e.g., ranchers) a prion-associated disease.

The RNA molecule may be added in a solution to the sample or immobilized on a solid support such as a membrane or filter to which the sample is added. It is contemplated that the RNA molecule may be provided in a kit and may be used alone or as a mixture, for example with other reagents which increase, enhance or stimulate the amplification of $PrP^{Sc}$. For example, the RNA molecule may be combined with detergents such as TRITON® (X-100 or X-114), TWEEN® (e.g., 20 or 80), BRIJ®, GENAPOL®, CHAPS, CHAPSO ZWITTERGENT® (e.g., 3-16, 3-14, 3-12, 3-10, or 3-8), THESIT®, sarkosyl, deoxycholate (e.g., sodium deoxycholate, sodium taurodeoxycholate, or sodium glycodeoxycholate), NP-40, sodium dodecyl sulfate, digitonin, or cetyltrimethylammonium bromide (CTAB); salts such as KCl, $MgCl_2$, or NaCl; buffers such as phosphate-buffered saline, tris-buffered saline, MOPS, HEPES, PIPES, Glycylglycine, MES or citrate buffer; chelating agents such as EDTA or EGTA; or other natural cofactors yet to be identified. Further examples are known by a person skilled in the art.

Further, the RNA molecule may be used alone or in combination with other methodologies of amplifying $PrP^{Sc}$ thereby improving said method. For example, an RNA molecule of the invention may be added to a homogenate of the methods of Saborio, et al. (2001) supra and Lucassen, et al. (2003) supra.

Moreover, factors such as temperature, ionic strength, pH-conditions, and the concentration of salt and non-ionic substances may be modified to further enhance the amplification of $PrP^{Sc}$ in the presence of the RNA molecule.

The step of identifying $PrP^{Sc}$ may be carried out using one or more methods well-known to those skilled in the art. Assays which may be used for detecting, measuring, quantifying or analyzing the levels or presence or absence of $PrP^{Sc}$ include, but are not limited to, western blot analysis (e.g., Prionics®-Check WESTERN), immunocapillary electrophoresis (ICE), immunocytochemistry, enzyme-linked immunosorbent assay (e.g., the commercially available assay of Enfer Scientific Ltd.), conformation-dependent immunoassay (InPro Biotechnology, San Francisco, Calif.) or a sandwich immunoassay (e.g. the diagnostic test of the French Atomic Energy Commission) which use antibodies which specifically recognize $PrP^{Sc}$, as well as those disclosed in WO 02/057789; WO 02/033420; WO 02/082919; WO 02/093168; U.S. Pat. Nos. 6,524,809; 6,316,607; 6,261,790; 6,165,784 for example.

It is contemplated that the method of identifying $PrP^{Sc}$ will be useful in providing diagnostic or predictive information pertaining to the presence of infectious prions in the individual from whom the sample was obtained. This method may be used to diagnose natural or experimental transmissible spongiform encephalopathies (TSEs) associated with infectious prions. TSEs which may be diagnosed include, but are not limited to, spongiform encephalopathy, feline spongiform encephalopathy, bovine spongiform encephalopathy (BSE), transmissible mink encephalopathy, scrapie, chronic wasting disease (CWD), sporadic Creutzfeldt-Jacob disease (CJD), iatrogenic CJD, variant CJD, atypical forms of CJD (e.g., ataxic CJD and Heidenhain's variant of CJD), kuru, Gerstmann-Sträussler-Scheinker disease, fatal familial insomnia, Alpers Syndrome or familial CJD.

A further aspect of the invention is a kit for identifying the presence of PrP$^{Sc}$. The kit includes a container holding one or more RNA molecules which enhance the amplification of PrP$^{Sc}$ and instructions for using the RNA molecule(s) for the purpose of amplifying PrP$^{Sc}$. The kit may be used in accordance with the method of the invention and may be used in combination with well-known methods or assays for detecting the presence PrP$^{Sc}$. Examples of containers include multi-well plates which allow simultaneous identification of PrP$^{Sc}$ in multiple samples.

As one of skill in the art may appreciate, the isolated RNA molecule or molecules which enhance the amplification of PrP$^{Sc}$ serve as ideal targets for therapeutic treatments of prion-associated diseases. Agents which target the RNA molecule or PrP$^C$ to block or promote the interaction between PrP$^C$ and the RNA molecule are expected to modulate the conversion of PrP$^C$ to PrP$^{Sc}$ or an infectious prion. Thus, it is contemplated that the RNA molecule may be used in binding studies or conversion assays with PrP$^C$ to screen for agents which block or promote the PrP$^C$-RNA molecule interaction. A readout for a conversion assay may include the binding of an antibody specific for PrP$^{Sc}$, wherein increases in the amount or rate of PrP$^{Sc}$ production is indicative of a stimulatory agent whereas decreases in the amount or rate of PrP$^{Sc}$ production is indicative of an inhibitory agent.

An agent which increases, enhances or stimulates the interaction between an RNA molecule and PrP$^C$, or the amount or rate of formation of PrP$^{Sc}$ produced, is useful in methods for enhancing the sensitivity of detecting PrP$^{Sc}$. An agent which decreases, inhibits or blocks the interaction between an RNA molecule and PrP$^C$, or the amount or rate of formation of PrP$^{Sc}$ produced, is useful for treating or preventing a prion-associated disease.

Such agents may be identified by screening a library of test agents. A library may comprise either collections of pure agents or collections of agent mixtures. Examples of pure agents include, but are not limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction may be assayed for the desired activity using the original assay until a pure, biologically active agent is obtained.

Library screening may be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotomers, calorimeters, and fluorimeters, and devices that measure the decay of radioisotopes.

Alternatively, inhibitory RNAs such as ribozymes, antisense RNA, RNAi, siRNA and the like may be designed to specifically interact with the RNA molecule of the present invention to decrease the activity or expression of the RNA molecule thereby decreasing its capacity to enhance the amplification of PrP$^{Sc}$. Inhibitory RNAs may be specific for sequences in the 5', 3' or middle of the RNA molecule. The target region may be selected experimentally or empirically. For example, siRNA target sites in a gene of interest may be 19-27 nucleotides in length, include an AA dinucleotide sequence at the 5' end and preferably have a G/C content of 30-50% (see, e.g., Elbashir, et al. (2001) *Nature* 411: 494-498).

As may further be appreciated by the skilled artisan, a transgenic non-human animal may be produced which overexpresses the RNA molecule of the present invention. Such a transgenic animal would be useful in methods of detecting the infectivity or in vivo transmission capacity of a sample suspected on containing an infectious prion. It is expected that such transgenic animals would produce a phenotype more rapidly than the currently available transgenic animals used for detecting PrP$^{Sc}$.

Not to be held to any particular mechanism of action, it is believed that an RNA molecule may specifically interact with specific prion strains thereby modulating prion transmission between species. Transgenic animals expressing compatible species-specific RNA molecules and PrP$^C$ would be useful in overcoming this species-specific barrier to detecting PrP$^{Sc}$ in a sample.

Furthermore, animals expressing the RNA molecule of the invention may be used for the more detailed characterization of prion-associated diseases to lead to elucidation of the pathogenesis of the progressive neurologic pathology and determination of the sequence of molecular events. The animals are useful for studying various proposed mechanisms of the pathogenesis of these diseases in order to lead to better treatments for the diseases.

Animals expressing the RNA molecule of the invention are also useful for the identification of previously unrecognized genes which may also play a role in prion-associated diseases, either beneficial or deleterious. A transgenic animal bearing a candidate gene is crossed with an animal expressing an RNA molecule of the invention and the effect of the presence of the candidate gene on the prion-associated disease-related traits of the transgenic animal are examined.

A candidate gene may be scored as beneficial if it delays or dilutes a prion-associated disease-related phenotype such as loss of motor control, dementia, paralysis wasting and death, typically following pneumonia.

Conversely, a candidate gene may be scored as favoring the development of a prion-associated diseases if it advances or enhances a disease-related phenotype.

It may further be appreciated that the identity of the RNA molecule or molecules provides a diagnostic or prognostic marker for individuals who may be more or less susceptible to acquiring, contracting or inheriting a prion-associated disease.

The invention is described in greater detail by the following non-limiting examples.

Example 1

Animal and Reagent Sources

Specific-pathogen-free 3-week old female Golden Syrian hamsters were obtained from Charles River Laboratories Wilmington, Mass.). Apyrase, DEPC, Cyclic 2',3'-GMP, 3'-CMP, heparinase III, heparan sulfate proteoglycan (MW>200,000), polyadenylic acid (MW 200,000-2,000,000), and polyglutamic acid (MW 50,000-100,000) were obtained from Sigma (St. Louis, Mo.). RNase-free DNase, micrococcal nuclease, RNase A, and DNase-free RNase were obtained from Roche (Indianapolis, Ind.). RNase T1 was obtained from EPICENTRE® (Madison, Wis.). Recombinant benzonase nuclease was purchased from NOVAGEN® (Madison, Wis.). EcoRI was obtained from GIBCO™ BRL (Carlsbad, Calif.). RNase H and RNase V1 were obtained from Ambion (Austin Tex.).

Example 2

In Vitro PrP$^{Sc}$ Amplification

In vitro PrP$^{Sc}$ amplification (Lucassen, et al. (2003) supra) and PMCA (Saborio, et al. (2001) supra) were performed as described, except that normal brain homogenates were prepared with EDTA-free Complete Protease inhibitors (Roche, Indianapolis, Ind.) to facilitate experiments involving metal-dependent enzymes. Two millimolar $MgCl_2$ was added to reactions with benzonase and 2 mM $CaCl_2$ was added to reactions with micrococcal nuclease and apyrase. All amplification and control reactions were performed at 37° C. for 16 hours. For PrP$^{Sc}$ detection, protease digestion was performed with 50 µg/ml proteinase K for 1 hour at 37° C. and immunoblotting was performed with 3F4 monoclonal antibody (Signet, Dedham, Mass.). All protein electrophoresis experiments were performed on 12% SDS polyacrylamide gels and reference relative molecular mass values ($M_r$) were given in kilodaltons (K).

Example 3

RNase A Inactivation

Pure RNase A (50 µg) was incubated with 1% DEPC in 100 µl at room temperature for 2 hours. Following incubation, the reaction was dialyzed twice against 1 L 10 mM Tris pH 7.2 at 4° C. using a 3500 MW SLIDE-A-LYZER® Mini dialysis unit (Pierce, Rockford, Ill.) to remove free DEPC. Control samples containing active RNase A were dialyzed in parallel. Protein recovery >90% was confirmed by BCA assay (Pierce, Rockford, Ill.).

Example 4

Nuclease Pretreatment of Brain Homogenates for Reconstitution Assays

Nuclease digestion prior to reconstitution was performed by incubating a batch of normal brain homogenate (10% w/v) with benzonase (final concentration of 2.5 units/µl) and 2 mM $CaCl_2$ for 16 hours at 4° C. in the absence of detergents. Benzonase was then inactivated by the addition of 5 mM EDTA prior to reconstitution with RNA or other polyanions.

Example 5

Preparation and Measurement of RNA

RNA was isolated from animals less than five minutes after sacrifice using rotor-stator homogenization, extraction with Trizol® reagent (INVITROGEN™, Carlsbad, Calif.), and isopropanol precipitation according to manufacturer's instructions, using RNase-free reagents, containers, and equipment. For yeast, cell walls were disrupted during extraction using well-established methods using Trizol® in place of phenol (Chapon, et al. (1997) *RNA* 3:1337-51). All RNA solutions were alcohol-precipitated, washed, and resuspended in RNase-free water prior to use. The concentration and purity of each solution was determined by spectroscopic measurement of optical density at $\lambda_1/\lambda_2$=260/280 nm and confirmed by agarose gel electrophoresis.

Example 6

RNA Size Fractionation

Total hamster brain RNA (0.4 mg) was diluted into 0.8 ml RNase-free water, loaded in 0.2 ml batches onto four separate Centrex UF-05 (100,000 MW cutoff) ultrafiltration devices (Schleicher and Schuell, Keene, N.H.), and centrifuged for 15 minutes at 3000×g. The devices were then washed with an equal volume of water. The filtrates were pooled and retentate fractions collected by briefly centrifuging the ultrafiltration devices upside-down into new microcentrifuge tubes. Parallel samples of denatured retentate were prepared in 50% formamide to disrupt all intra- and inter-molecular interactions.

Total RNA was also fractionated using oligo dT column chromatography. Three milligrams of total hamster liver RNA was applied to a single QIAGEN® Mega OLIGOTEX® column according to manufacturer's instructions. RNA isolated from the column included poly A– (flow-through) and poly A+ (eluate). PrP$^{Sc}$ amplification of a mixture of 0.05% hamster scrapie brain homogenate and 10% normal hamster brain homogenate was conducted in the presence of poly A–, poly A+ or total RNA each at a final concentration of 0.5 mg/ml. Amplification was carried out at 37° C. for 16 hours prior to Proteinase K digest.

Size separation of the poly A– RNA was conducted on a 5-35% sucrose gradient using standard methods. Fractions from the gradient were separated on a 1% agarose gel stained and stained with ethidium bromide. 0.5 mg/ml of poly A– RNA precipitated from each gradient fraction was included in PrP$^{Sc}$ amplification experiments.

Example 7

Purification of PrP$^C$ for Use as a Substrate

PrP$^C$ was purified from normal hamster brains, using a modification of the method of Pan, et al. ((1993) *Proc. Natl. Acad. Sci. USA* 90(23):10962-6). Briefly, hamster brain tissue was homogenized in 0.3 M sucrose and microsomes were isolated by differential centrifugation. The microsomal pellet was solubilized in 1.5% CHAPSO and PrP$^C$ was purified by affinity chromatography on IMAC-Cu and wheat germ agglutinin columns eluted with buffers containing imidazole and N-acetylgluosamine, respectively. After solubilization, the detergent present in the PrP$^C$ preparation was changed to 1% TRITON X-100; thus, the PrP$^{Sc}$ amplification assay contained 0.5% TRITON X-100 (final concentration).

Samples containing either crude hamster brain homogenate (5% w/v) or chromatographically purified PrP$^C$ were mixed with 0.1% Sc237 scrapie brain homogenate overnight at 37° C. Duplicate samples were prepared which further contained 0.01 U/µL RNase A or 0.5 mg/mL total hamster brain RNA. Control samples contained 0.1% scrapie brain homogenate alone and all samples were subjected to protease digestion and western blot analysis to detect PrP$^{Sc}$.

What is claimed is:

1. An isolated RNA fraction that enhances the amplification of PrP$^{Sc}$, said RNA fraction obtained by:
   (a) isolating RNA from non-human mammalian brain tissue;
   (b) passing the RNA through an oligo dT column to obtain a fraction of RNA that does not to bind to the oligo dT column; and
   (c) separating the fraction of RNA of (b) by ultrafiltration to obtain a fraction of RNA of greater than 300 nucleotides.

2. A kit for identifying the presence of PrP$^{Sc}$ comprising the RNA fraction of claim 1.

* * * * *